United States Patent [19]
Pomerantzeff

[11] Patent Number: 4,699,480
[45] Date of Patent: Oct. 13, 1987

[54] SURGICAL OPHTHALMOSCOPES

[75] Inventor: Oleg Pomerantzeff, Brookline, Mass.

[73] Assignee: Eye Research Institute of Retina Foundation, Boston, Mass.

[21] Appl. No.: 867,804

[22] Filed: May 27, 1986

Related U.S. Application Data

[63] Continuation of Ser. No. 583,247, Feb. 24, 1984, abandoned.

[51] Int. Cl.⁴ .................... A61B 3/10; G02B 21/22
[52] U.S. Cl. ...................... 351/205; 350/410
[58] Field of Search .............. 351/205, 20.6, 207, 351/208; 350/410, 516, 514, 515

[56] References Cited

U.S. PATENT DOCUMENTS

| | | | |
|---|---|---|---|
| 1,095,285 | 5/1914 | Oliver | 350/518 X |
| 2,437,775 | 3/1948 | Williams | 350/518 X |
| 2,765,702 | 10/1956 | Sachtleben | 351/205 |
| 3,202,050 | 8/1965 | Seidenberg | 350/410 |
| 3,475,082 | 10/1969 | Strietzel | 351/6 |
| 3,582,191 | 6/1971 | Cohen et al. | 351/16 |
| 3,945,712 | 3/1976 | Crock et al. | 351/6 |
| 3,963,329 | 6/1976 | Stumpf et al. | 351/6 |
| 4,248,505 | 2/1981 | Muchel et al. | 351/7 |
| 4,448,498 | 5/1984 | Muller et al. | 350/518 X |

*Primary Examiner*—Rodney B. Bovernick
*Attorney, Agent, or Firm*—Lahive & Cockfield

[57] ABSTRACT

A surgical ophthalmoscope for observing the fundus of a patient's eye, the ophthalmoscope having a left eyepiece and a right eyepiece, a light source for directing light into the patient's eye, a condensing lens for focusing an image of the patient's eye in a focal plane perpendicular to an optical axis, a telescopic tube, an image-interchanging device for splitting the image into a left image and a right image and then interchanging the images such that image rays entering the right side of the condensing lens are directed to a right optical path, while image rays from the left side are directed to a left optical path, and left and right magnifying devices, each including an objective lens and an ocular lens situated between the image-interchanging device and the eyepieces in optical alignment to magnify the interchanged images and to transmit the magnified images to the respective eyepieces.

11 Claims, 6 Drawing Figures

SURGICAL OPHTHALMOSCOPES

This application is a continuation of application Ser. No. 583,247, filed Feb. 24, 1984 now abandoned.

BACKGROUND OF THE INVENTION

This invention relates to ophthalmological instruments and, in particular, to magnifying ophthalmoscopes useful in surgery on the fundus or retina of a patient's eye.

A number of instruments are known for examination of the fundus of the eye. The direct ophthalmoscope is typically a hand-held instrument which illuminates but does not actually magnify the fundus. The image seen is erect rather than inverted, and the practitioner must position his or her eye in close proximity to the instrument and the patient. Moreover, the image has a narrow field of view and it lacks depth because it is focused with only one of the examining practitioner's own eyes. For these reasons, the direct ophthalmoscope is unsuitable for surgical use.

Another examining instrument is the indirect ophthalmoscope, which uses a magnifying lens, called a condensing or observation lens. This lens is placed in front of the patient's eye and is used to focus a magnified image of the fundus at an image plane located between the patient and the observer for stereo viewing. The condensing lens typically is used in conjunction with a binocular device, supported upon the practitioner's head, which reduces the practitioner's interpupilliary distance and provides illumination. However, the fundal image viewed by the practitioner is inverted and reversed, and this condition is unacceptable to the surgeon because of the need for precision and the chance of reflexive errors.

In an operating room, surgery on the fundus is typically performed with a flat contact lens sutured to the conjunctiva of the patient's eye. A slit lamp or surgical microscope positioned above the patient illuminates the fundus and focuses the fundal image transmitted by the patient's cornea and the contact lens. The contact lens is employed to cancel the strong refraction of the cornea, but can interfere with surgical activities. The contact lens also can cause edema of the corneal epithelium, as well as make detailed observation of the peripheral vitreous and retina more difficult or impossible. Moreover, the surgical microscope has disadvantages in use; the brightness of the fundal image decreases with increasing magnification. Insufficient brightness reduces the visibility, contrast and resolution of the image.

Another instrument, described as a stereo funduscope, is disclosed in U.S. Pat. No. 3,475,082 issued to Strietzel. This device operates with a condensing lens in manner similar to the indirect ophthalmoscopes described above, and employs a series of lenses to provide further magnification and to reverse the fundal images to an erect orientation in the eyepieces. A separating prism and a second prism switch the images transmitted to the left and right eyepieces in order to maintain proper stereopsis. This instrument is considered to suffer from significant operational constraints. As described in the patent, the distance between the condensing lens and the pupil of the patient's eye must be fixed by spacers resting against the patient's forehead. Further, the location of the condensing lens must correct for refractive errors of the patient's cornea so that the intermediate image of the fundus is focused precisely at the apex of the separating prism.

There accordingly exists a need for surgical ophthalmoscopes which can provide better magnification and good resolution, particularly to perform operations on the retina and around the macula of the eye. Such instruments desirably are to provide an erect view without sacrificing proper stereopsis and without sacrificing a substantial portion of the field of view; they hence are to maintain depth perception and enable viewing of nearly the entire fundus. Moreover, a surgical ophtalmoscope that can be operated without a contact lens and without spacers that might interfere with a surgeon's range of motion would satisfy a long-felt need.

SUMMARY OF THE INVENTION

The present invention resides in an improved surgical ophthalmoscope providing magnified stereo images of a patient's eye fundus. The instrument has a condensing lens, a pair of magnifying (Keplerian) telescopes and two sets of image-interchanging mirrors which transmit the fundal image from the condensing lens to the magnifying optics. This instrument provides erect images, achieves magnification and maintains stereopsis, without significant losses in either illumination or field of vision. In a preferred embodiment, the ophthalmoscope is a compact, stand-mounted, instrument which can be placed above the patient's eye to provide fundal images to the surgeon during an operation.

In conventional indirect ophthalmoscopes, mangifying power is limited by the hand-held condensing lens. A condensing lens will magnify not only the image seen by the practitioner but also the image of the light source in the patient's pupillary plane. A limit is reached either when the magnified image of the light source leaves no room in the patient's pupil for the practitioner to observe the fundal image, or when the light source is partially cut by the patient's iris thereby reducing the brightness of the fundal image. Practically this limit generally is in the order of 5×. The present invention solves the is problem by incorporating telescopes into the ophthalmoscope eyepieces, in a manner that increases magnification of the fundal images without affecting the magnification of the light source.

An opthalmoscope according to a preferred embodiments of the invention employs Keplerian rather than Galilean telescopes. Keplerian magnifying optics provide a significantly larger field of vision to the practitioner. Such a Keplerian system (i.e., having positive oculars) with 6× magnification yields a field of view of about 42 degrees, and a similar 10× Keplerian system yields a field of about 33 degrees. In comparison, a Galilean system (i.e., having negative oculars) would yield only about an 8 degree field under 6× mangification.

The Keplerian telescopes incorporated into each eyepiece in accordance with the invention create inverted, reversed images in the observer's eyes. The practitioner therefore sees an erect image of the fundus when the magnifying optics and condensing lens are used together. However, since the condensing lens acts first to interchange the right and left images of the surgeon's pupils, the erect images of the fundus would be seen by the surgeon's with pseudosteropsis. To restore the stereopsis, the images focused in the left and right eyepieces must be interchanged again.

The present invention solves this further problem by providing the Keplerian magnifying subassemblies and a cooperating image-interchanging subassembly, operating in tandem on the left and the right images, to interchange and then magnify the images from the condensing lens. In one preferred embodiment, the image-interchanging subassembly consists of a left image set and a right image set of parallel mirrors, offset from each other along the optical axis so that the left and right images do not interfere as they are interchanged. In this embodiment, a left leading mirror reflects the left side of the image from the condensing lens to right where it is reflected again into the magnifying optics of the right side of the instrument. Similarly, a right mirror positioned rearward of the left mirror reflects the left side of the image from the condensing lens into the magnifying optics of the left side of the instrument.

In addition, the invention can include a mechanism for adjusting the position of the mirrors to match the practitioner's interpupilliary and observation distances. Moveover, the invention can include a means for adjusting the angle of the illuminating light and the degree of magnification. In one preferred embodiment, the location of the objective lenses also is adjustable by a mechanism to provide so-called "zoom" focusing control.

The preferred embodiments of the invention will next be described in detail; however, it should be clear that various changes and modifications may be made by those skilled in the art without departing from the spirit or scope of the invention. For example, various equivalent mechanisms can be constructed to replace the adjustment mechanisms (e.g., cam mechanisms, pivoting mechanisms and translations stages) described hereinafter.

BRIEF DESCRIPTION OF THE DRAWINGS

FIG. 4 is a top view of an image-interchanging subassembly for the instrument of FIGS. 3 and 3a, and FIG. 5 is a bottom view of the zoom control mechanism for the instrument of FIGS. 3 and 3a.

DETAILED DESCRIPTION OF THE PREFERRED EMBODIMENTS

Figure 1:
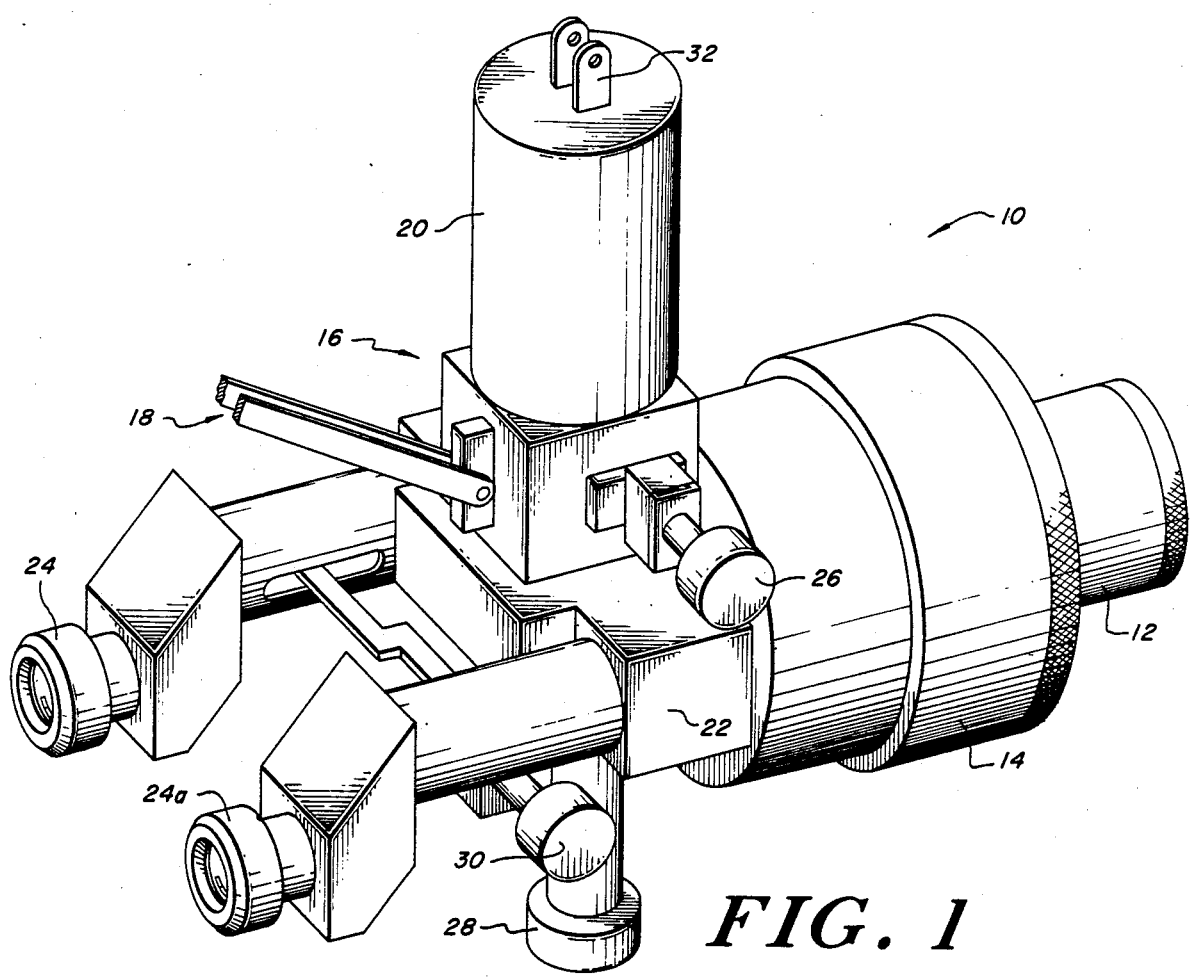
FIG. 1 is an overall, perspective view of an ophthalmoscope according to the present invention.

FIG. 1 shows an overall view of an ophthalmoscope 10 according to the invention and having a built-in condensing lens 12, a telescopic tube 14 and a viewing instrument 16. The ophthalmoscope is adapted to be mounted above a patient undergoing surgery. The instrument 16 includes a support bracket 18, a lump body 20 and an optical assembly 22. The instrument 16 also includes an aperture 64 (shown in FIG. 3 and 3A) through which images are received from the condensing lens 12, and eyepieces 24 and 24a for binocular viewing. Additionally, the instrument 16 has an adjustment knob 26 for adjusting the angle of illumination, and another adjustment knob 28 to adjust for the size of the patient's pupil as well as a zoom control 30 to adjust the magnification. Electrical connector 32 provides the electrical contacts for a battery or other power supply (not shown) for the illuminating lamp.

Figure 2:
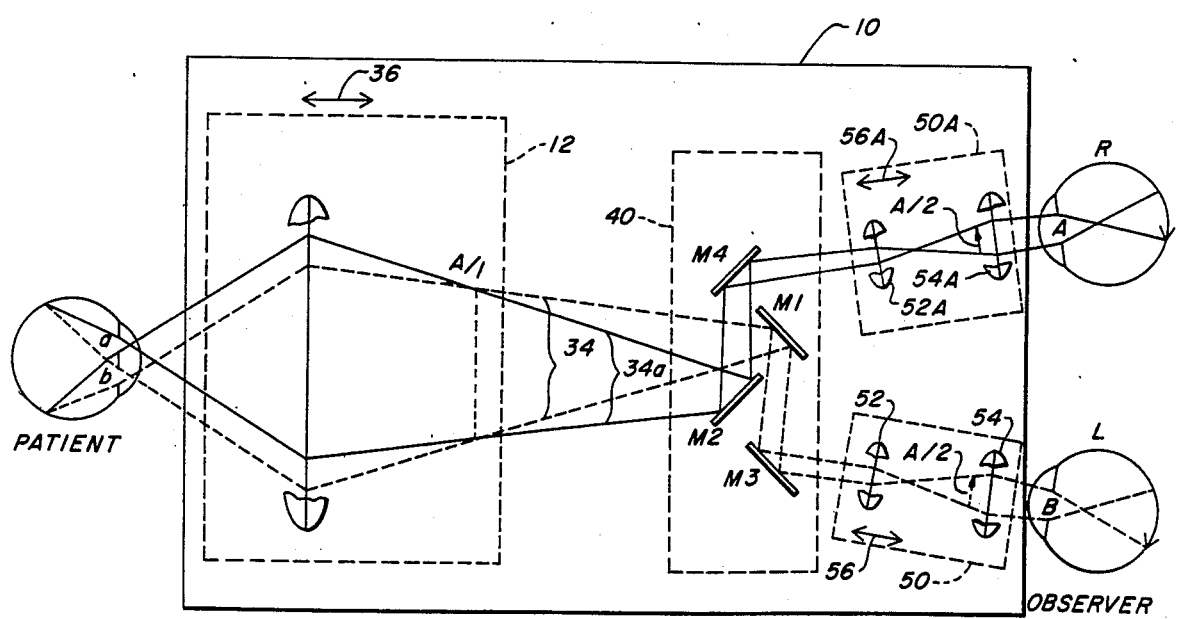
FIG. 2 is a schematic drawing of the imaging optics of the opthalmoscope of FIG. 1.

In FIG. 2 the optical imaging path is shown schematically. A left optical path 34, shown by dotted lines, is defined by the condensing lens 12, mirrors M1 and M3 of an image-interchanging subassembly 40, and the left magnifying subassembly 50. A right optical path 34A, shown in solid lines, is defined by condensing lens 12, mirrors M2 and M4 of the image-interchanging subassembly 40, and a right magnifying subassembly 50A. Condensing lens 12 focuses an image of the patient's fundus in air at focal plane A/1. This image is inverted, top to bottom and left to right. Subassembly 40 interchanges the left-sided and right-sided image rays from the condensing lens 12 in order to avoid the condition of pseudo stereopsis. The switched left and right views are then passed to the magnifying subassemblies 50 and 50A. The image is refocused at a pair of focal planes A/2 by the objective lenses 52, 52A of magnifying subassemblies 50 and 50A. The end result seen through the ocular lenses 54, 54A is thus a magnified, erect image with proper stereopsis.

The focus of the ophthalmoscope is adjusted by forward or rearward movement of the condensing lens 12 as shown by arrow 36. This movement can be accomplished by sliding the telescopic tube forward or rearward 14 shown in FIG. 1 relative to the patient's eye. Additionally, the mirrors M1 and M2 can be adjusted forward and rearward as shown by arrow 43 using the adjustment knob 28 shown in FIGS. 3 and 4. Movement of mirrors M1 and M2, e.g., by a rack and pinion drive, while mirrors M3 and M4 remain stationary, permits one to change the observer's interpupilliary distance and thus accommodate different observation distances and variations in the patient's pupil size.

The images from the mirrors M3 and M4, respectively, are transmitted to the left and right magnifying subassemblies 50 and 50A, which each include objective lenses 52, 52A and ocular lenses 54, 54A, respectively. Intermediate between the objective and ocular lenses of each magnifying subassembly are first and second periscopic mirrors 74, 76, 74A, 76A, respectively, (shown in FIG. 3a) which provide a further separation between the objective and ocular lenses of each assembly and permit adjustments for variations in the observer's interpupilliary distance by rotation.

Figure 3:
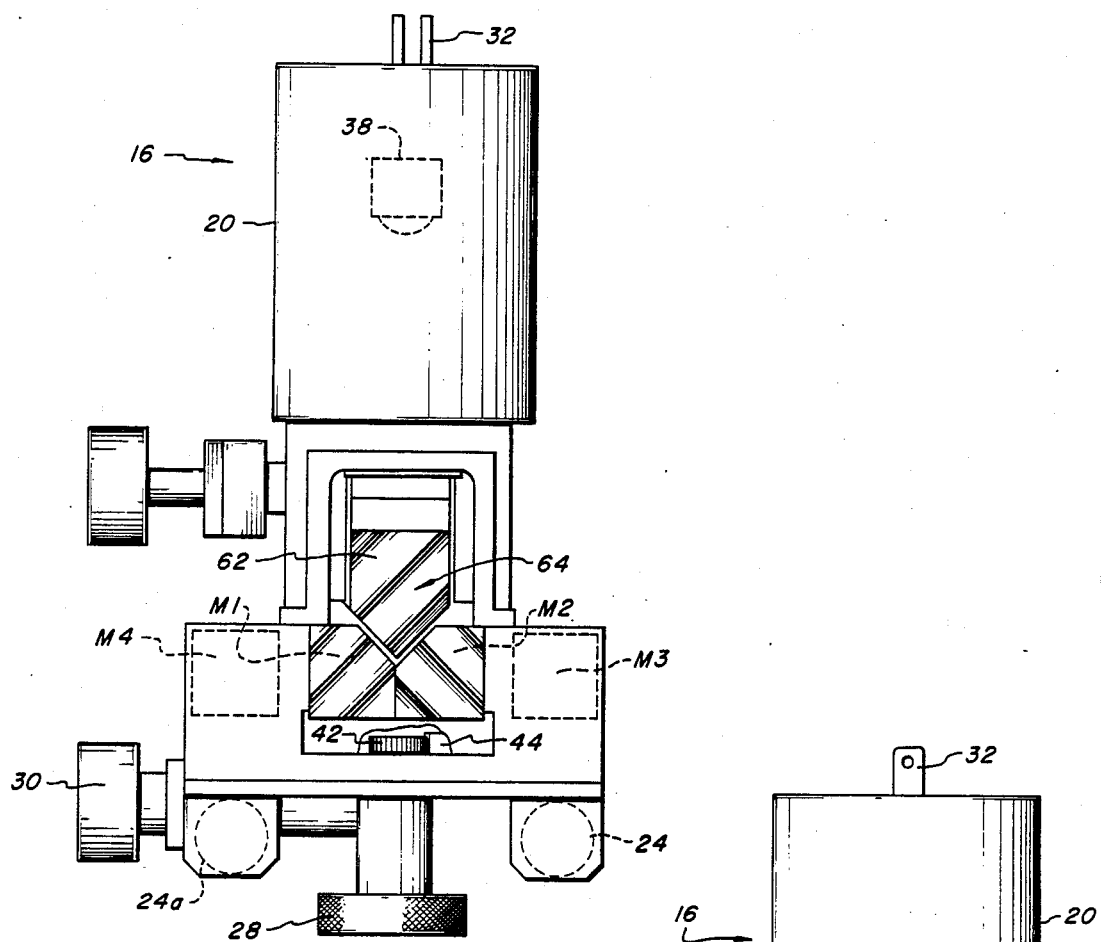
FIGS. 3 and 3a are front and side views, respectively, of the body of an ophthalmoscopic instrument according to the present invention.
Figure 3A:
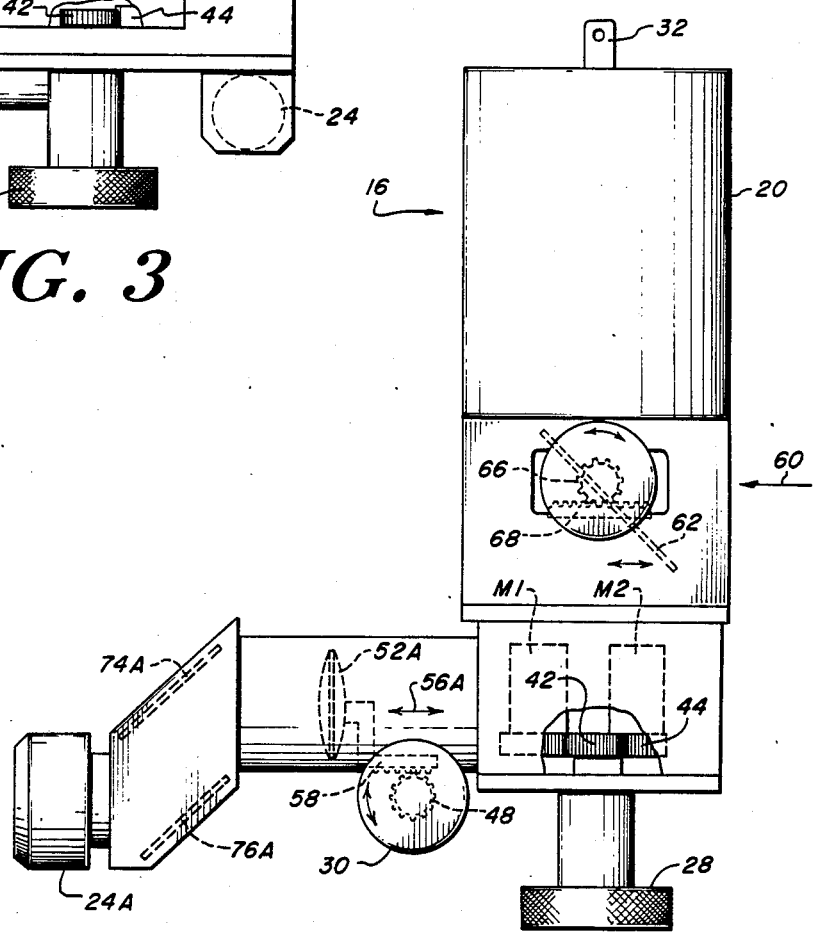
Figure 5:
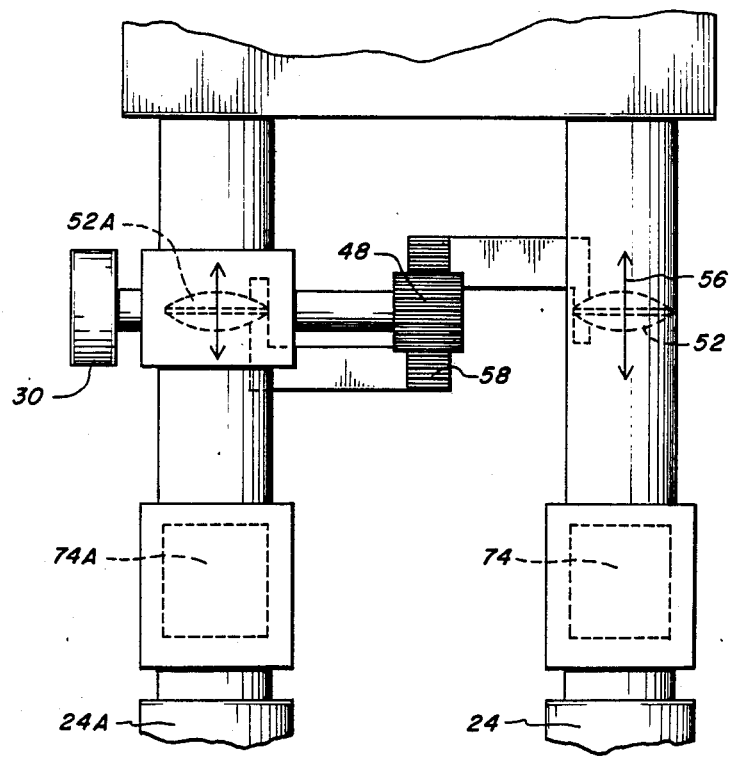

The positions of the objective lenses 52 and 52A relative to their respective ocular lenses 54 and 54A can be adjusted forward and rearward along the left and right optical paths, as shown by arrows 56 and 56A, using the zoom control 30 shown in FIGS. 3A and 5. In the illustrated embodiment, the control 30 employs a pinion gear attached by a rack to both objective lenses 52 and 52A. Turning the knob thus provides a mechanism to translate the position of the objective lenses 52 and 52A fore and aft, along optical path 60. Additionally, in the preferred embodiment, the ocular lenses 34 and 34A are individually adjustable, e.g., by rotation in a threaded housing, to match the practitioner's refraction and thus provide sharper focus.

FIGS. 3 and 3a show that the lamp body 20 of the instrument 16 of FIG. 1 houses a lamp 38 which can be connected to a conventional battery pack or other source of electric power (not shown) via electrical plug 32. When the lamp is on, light is reflected off the illumination mirror 62 and out of aperture 64 to the condensing lens (FIG. 2) and from there to the inside of the patient's eye. The angle of illumination is adjusted by knob 26, i.e. rotation of knob 26 causes pinion gear 66 engaged in rack 68 to move mirror 62 forwards or rearwards along the optical axis 60.

Figure 4:
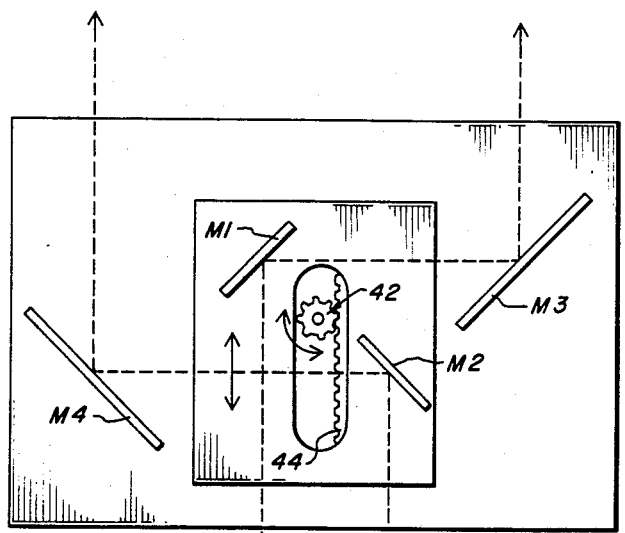

Image rays returning from the patient's eye pass back through the condensing lens, and upon entering aperture 64 are split by mirrors M1 and M2 and reflected off mirrors M3 and M4 such that the left and right images are switched and passed to the eyepieces as discussed above. Knob 28 is connected to a pinion gear 42 which engages a rack 44 across which are seated the mirrors M1 and M2. As shown in FIG. 4, rotation of knob 28 activates the rack and pinion mechanism and causes mirrors M1 and M2 to move forward or backward.

The zoom control of objective lenses 52 and 52A is shown in FIGS. 3 and 3a and particularly in FIG. 5. Knob 30 on the side of the instrument 16 is connected to the pinion gear 48. This gear 48 engages a rack 58 upon which the objective lenses 52 and 52A are seated. Rotation of knob 30 thus causes the objective lenses 32 and 32A to move forward and back.

The foregoing combination of an adjustable condensing lens, image-interchanging means, and magnifying optics in a compact, adjustable instrument thus provides an substantial contribution to the field of ophthalmoscopic instruments. It should be clear that various changes and modifications can be made by those skilled in the art without departing from the spirit or scope of the invention.

What is claimed is:

1. A surgical ophthalmoscope for observing the fundus of a patient's eye, said ophthalmoscope having a left eyepiece and a right eyepiece, a light source and means for directing light from the light source into the patient's eye, and having the improvement comprising
   A. an adjustable condensing lens for focusing a single image of the patient's eye in a variable focal plane perpendicular to an optical axis, said axis being defined by the path of the light reflected by the patient's eye,
   B. image-interchaning means for splitting said single image into a left image and a right image and for interchanging said left and right images such that image from the right side of the condensing lens is directed to the right eyepiece and image from the left side of the condensing lens is directed to the left eyepiece, the image-interchanging means comprising first and second reflective means, each reflective means having a leading reflective surface and a further reflective surface in optical alignment, said reflective surfaces of said first and second reflective means cooperating to split said single image and interchange said left and right images, the leading reflective surfaces being offset from each other along the optical axis, and the further reflective surfaces being offset from each other along the optical axis, and
   C. left and right magnifying means, each comprising an adjustable objective lens and an ocular lens, each said magnifying means being situated between the image-interchanging means and the respective eyepiece and disposed in optical alignment therewith for magnifying the interchanged images and to transmit the images to the respective eyepieces.

2. An ophthalmoscope according to claim 1 further comprising means providing adjustable movement, along the optical axis, of each leading reflective surface of each reflective means relative to the further reflective surface of that reflective means.

3. An ophthalmoscope according to claim 1 wherein each magnifying means comprises a pair of periscopic reflecting means arranged in optical alignment between the objective lens and the ocular lens.

4. An ophthalmoscope according to claim 3 wherein said periscope means are rotatable to accomodate variation in the interpupilliary distance of the user.

5. An ophthalmoscope according to claim 1 having the further improvement comprising means for adjusting the position of the image-interchanging means along the optical axis.

6. An ophthalmoscope according to claim 1 wherein the means for directing light comprises means for adjusting the angle along which the light is directed.

7. An ophthalmoscope according to claim 1 further comprising a telescopic tube connecting the condensing lens to the image-interchanging means.

8. A stereoscopic ophthalmoscope for observing the fundus of a patient's eye, the ophthalmoscope having a left eyepiece and a right eyepiece, a light source and a means for directing light from the light source into the patient's eye, said ophthalmoscope further comprising
   A. an adjustable condensing lens for focusing a single image of the patient's eye in a variable focal plane perpendicular to an optical axis, said axis being defined by the path of the light reflected by the patient's eye,
   B. an adjustable image-interchanging means disposed along said optical axis for splitting the single image into a left image and a right image, and interchanging said left and right images such that image from the right of the condensing lens is directed to the right eyepiece and image from the left of the condensing lens is directed to the left eyepiece, the image-interchanging means comprising two parallel reflective means offset from each other for accommodating variations in the axial location of said focal plane and each reflective means having a leading mirror surface adapted for movement in the forward and rearward directions along the optical axis,
   C. left and right magnifying means, each comprising an adjustable objective lens and an ocular lens, and each magnifying means being situated between the image-interchanging means and its respective eyepiece and disposed in optical alignment therewith to magnify the respective interchanged images and transmit them to the respective eyepieces, said left and right magnifying means further comprising means for adjusting the positions of the objective lenses forward and rearward in relation to their respective ocular lenses, and
   D. means for adjusting the angle of light directed from the light source into the patient's eye.

9. A stereoscopic opthalmoscope according to claim 8 in which each of said left and right magnifying means further comprises a pair of perioscopic reflective means, each pair being arranged between the objective lens and the ocular lens of the respective magnifying means.

10. A method for examining the fundus of a patient's eye with a light source and a condensing lens, said method comprising the steps of
    A. directing light from the light source into the patient's eye,
    B. condensing an image of the fundus of the patient's eye at a focal plane perpendicular to an optical axis defined by the path of the light reflected by the patient's eye,
    C. splitting the image from the condensing lens into a left image and a right image, by employing first and second leading reflective surfaces offset from each other along the optical axis, D. interchanging the split left and right images, by employing third and fourth further reflective surfaces in conjunction with said first and second reflective surfaces, E. adjusting the placement of said first and second reflective surfaces along the optical axis relative to the placement of said third and fourth reflective surfaces for compensating for different observation distances and for variations in the pupil size of the patient's eye, F. magnify the respective interchanged images in a pair of left and right magnifying means and G. focusing at an image plane, with said magnifying means, the magnified images to present a stereoscopic and magnified view of the fundus of the patient's eye.

11. A surgical ophthalmoscope for observing the fundus of a patient's eye, said ophthalmoscope having a left eyepiece and a right eyepiece, a light source and means for directing light from the light source into the patient's eye. and having the improvement comprising A. an adjustable condensing lens for focusing a single image of the patient's eye at a variable focal plane perpendicular to an optical axis defined by the path of the light reflected by the patient's eye, B. image-interchanging means for splitting said single image into a left image and a right image and for interchanging said left and right images such that image from the right of the condensing lens is directed to the right eyepiece and image from the left of the condensing lens is directed to the left eyepiece, said image-interchanging means comprising first and second reflective means, each reflective means having a leading reflective surface in optical alignment with a further reflective surface and having means for adjustably positioning said leading reflective surface of each first and second reflective means along the optical axis relative to said further reflective surface of that reflective means.

* * * * *